(12) United States Patent
Patel et al.

(10) Patent No.: US 9,616,128 B2
(45) Date of Patent: Apr. 11, 2017

(54) PHARMACEUTICAL COMPOSITIONS COMPRISING PARACETAMOL AND PROCESS FOR PREPARING THE SAME

(75) Inventors: Ketan R. Patel, Gujarat (IN); Milan R. Patel, Gujarat (IN); Prakashchandra J. Shah, Gujarat (IN)

(73) Assignee: Troikaa Pharmaceuticals Ltd, Ahmedabad (IN)

( * ) Notice: Subject to any disclaimer, the term of this patent is extended or adjusted under 35 U.S.C. 154(b) by 320 days.

(21) Appl. No.: 13/806,541

(22) PCT Filed: Jun. 29, 2011

(86) PCT No.: PCT/IB2011/001519
§ 371 (c)(1),
(2), (4) Date: Dec. 21, 2012

(87) PCT Pub. No.: WO2012/001494
PCT Pub. Date: Jan. 5, 2012

(65) Prior Publication Data
US 2013/0096201 A1    Apr. 18, 2013

(30) Foreign Application Priority Data

Jun. 30, 2010 (IN) .......................... 3023/MUM/2009
Sep. 9, 2010 (IN) ............................ 630/MUM/2010

(51) Int. Cl.

| | | |
|---|---|---|
| A61K 47/22 | (2006.01) | |
| A61K 47/10 | (2006.01) | |
| A61K 47/02 | (2006.01) | |
| A61K 9/00 | (2006.01) | |
| A61K 31/167 | (2006.01) | |

(52) U.S. Cl.
CPC ............ *A61K 47/22* (2013.01); *A61K 9/0019* (2013.01); *A61K 31/167* (2013.01); *A61K 47/02* (2013.01); *A61K 47/10* (2013.01)

(58) Field of Classification Search
None
See application file for complete search history.

(56) References Cited

U.S. PATENT DOCUMENTS

| | | | | |
|---|---|---|---|---|
| 6,028,222 | A * | 2/2000 | Dietlin et al. ................... | 564/4 |
| 2003/0152637 | A1* | 8/2003 | Chasin ................ | A61K 9/0024 |
| | | | | 424/501 |
| 2006/0052757 | A1* | 3/2006 | Fischer, Jr. ............... | A61F 2/82 |
| | | | | 604/265 |

FOREIGN PATENT DOCUMENTS

| | | |
|---|---|---|
| IN | 2008 MU 01746 | 2/2010 |
| WO | 0007588 | 2/2000 |
| WO | 0108662 | 2/2001 |
| WO | 2009047634 | 4/2009 |

OTHER PUBLICATIONS

Granberg et al. Journal of Chemical and Engineering Data 1999 44(6):1391-1395.*
Vromans H et al: "Effects of solvents on rectal absorption rate of paracetamol in man: an in vitro approach", International Journal of Pharmaceutics, vol. 26, No. 1-2, Sep. 1, 1985 (pp. 5-13).
Chemical Abstracts Service, Columbus, Ohio, US; Chimanlal, Shah Arun et al: "A pharmaceutical formulation for paracetamol injection".

* cited by examiner

*Primary Examiner* — Robert A Wax
*Assistant Examiner* — Caralynne Helm
(74) *Attorney, Agent, or Firm* — Bay State IP, LLC

(57) ABSTRACT

Disclosed herein are injectable compositions containing high concentration of paracetamol or its pharmaceutically acceptable salts wherein the concentration of paracetamol or its pharmaceutically acceptable salt is >150 mg/ml in a judiciously tailored solvent system comprising glycofurol, ethanol, water or a solvent system comprising glycofurol, ethanol, polyethylene glycol, water. The viscosity of the said injectables is <28 cps. Further disclosed is the process for preparing the said injectables. The injectables can be administered by intramuscular route, intravenous route or as intravenous infusion after diluting in one of the routinely used intravenous fluids, infusion solutions of antibacterial, antifungal and amoebicidal drugs and along with anxiolytics (Midazolam injection) or narcotic analgesics (Fentanyl Citrate injection etc) as they remain stable, clear and transparent at least for 6 hours after dilution.

15 Claims, No Drawings

PHARMACEUTICAL COMPOSITIONS COMPRISING PARACETAMOL AND PROCESS FOR PREPARING THE SAME

CROSS REFERENCE TO RELATED APPLICATION

This application is for entry into the U.S. National Phase under §371 for International Application No. 13806541 having an international filing date of Jun. 29, 2011, and from which priority is claimed under all applicable sections of Title 35 of the United States Code including, but not limited to, Sections 120, 363, and 365(c), and which in turn claims priority under 35 USC 119 to India Patent Application No. 3023/MUM/2009 filed on Jun. 30, 2010 and No. 630/MUM/2010 filed on Sep. 9, 2010.

RELATED APPLICATION

The invention disclosed in Indian Patent Application No. 630/MUM/2010, filed on Sep. 9, 2010, is cognate with the invention disclosed in Indian Patent Application No. 3023/MUM/2009 filed on Jun. 30, 2010, in a way that they constitute a single invention.

FIELD OF THE INVENTION

The present invention relates to parenteral compositions of paracetamol containing therapeutically effective dose of paracetamol, process for preparation thereof including therapeutic use of the said compositions.

BACKGROUND OF THE INVENTION

Paracetamol (p-acetylaminophenol) is a common analgesic and antipyretic drug that is used for the relief of fever, headaches, and other minor aches and pains. It is a major ingredient in numerous cold and flu medications and many analgesics prescriptions. The drug is popularly used as an analgesic and antipyretic, and as a pain reliever in acute pain and chronic pain. Paracetamol injections are used for the management of acute febrile conditions as well as analgesic for management of acute pain including post operative pain.

Pharmaceutical preparations comprising paracetamol to be administered orally are well known. It is however well accepted that concentrated parenteral pharmaceutical compositions containing paracetamol in solution offer several advantages over solid compositions as they provide rapid onset of pharmacologic action, since, unlike the oral compositions, which first have to first disintegrate and dissolve in the gastrointestinal tract to enable absorption.

There are two classes of conventional parenteral formulations of paracetamol available in the market.

The first one comprises 150 mg/ml paracetamol presented in 2 ml solution. This dosage form provides 300 mg of paracetamol per dose which is much below the minimum therapeutic dose of 500 mg. These have high viscosity of about 24.80 cps causing pain when administered by the intramuscular route. Further this dosage form has the additional disadvantage of delivering sub-therapeutic quantities.

The other parenteral formulation comprises aqueous solutions of paracetamol in a concentration of 10 mg/ml, presented in 50 ml and 100 ml vials providing 500 mg and 1000 mg of paracetamol per vial respectively. These dosage forms are administration only by intravenous infusion and obviously unsuitable for intramuscular route. Such dosage forms are not suitable for use in Out-Patient-Department (OPD) settings. Concurrent administration of these dosage forms with other intravenous fluids, e.g. Ciprofloxacin I.V. infusion, is inconvenient. Further, manufacture of these dosage forms need additional infrastructure, larger storage space and bulk transport adding to the end cost of these products.

There is therefore an unmet need to provide high concentration paracetamol containing injectable compositions that can deliver the therapeutic dosage (500 mg) in single dose for intramascular administration without causing pain to the patient. Further there is a need for such high concentration dosage forms that can be adapted for administration with I.V. infusions PCT/IN2009/000038 relates to aqueous, stable pharmaceutical composition comprises paracetamol for parenteral administration, wherein the concentration of paracetamol in the composition is 10 mg/1 ml. The dosage form is suitable only for intravenous infusion.

PCT/IB2008/003217 discloses stable aqueous formulations containing 10 mg/1 ml of acetaminophen exclusively to be administered by intravenous infusion as well as processes for their preparation.

PCT/NL2004/000819 relates to a composition with the aqueous state for the administration in perfusion of at least an active principle, especially pharmacological such as paracetamol.

PCT/GR2001/000047 discloses stable solutions of paracetamol for parenteral administration wherein the concentration of paracetamol is 150 mg/1 ml. These need to be administered in multiple doses to achieve the therapeutic dosage of 500 mg and hence are not suitable.

PCT/EP1999/005486 describes a pharmaceutical composition, characterized in that: a) it comprises i) paracetamol, ii) from 1 to 4 parts by volume of a low molecular weight alcohol for each part by weight of paracetamol, and iii) from 1 to 5 parts by volume of a polyethylene glycol for each part by weight of paracetamol; b) it is substantially anhydrous; and c) it forms a clear solution for injection with 4-10 parts by volume of water for each part by weight of paracetamol. The solutions disclosed are "substantially anhydrous" which, as disclosed in the said patent, is understood to mean a composition containing less than 0. 1% by weight of water. The solutions disclosed are expected to be very viscous. Hence, these solutions are to be diluted with water to provide the injection solution wherein each part by weight of paracetamol has, i) from 1 to 4 parts by volume of a low molecular weight alcohol, ii) from 1 to 5 parts by volume of a polyethylene glycol, and iii) from 4 to 10 parts by volume of water.

Example number 1 of the said patent describes the preparation of the concentrated anhydrous solution which has a paracetamol titer of about 210 mg per ml. Example number 2, describes dilution of this concentrated anhydrous solution to produce injection solutions. As calculated, the titer of paracetamol in the injection solutions is about 85.60 mg per ml of injection solutions.

PCT/IB2008/003925 relates to stable aqueous solution of paracetamol containing about 10 mg/1 ml, to be administered exclusively by intravenous infusion.

PCT/US2008/083458 relates to compositions containing 10 mg/ml of Paracetamol for exclusive, administration by intravenous infusion.

PCT/EP2002/011498 relates to ready-to-use highly stable paracetamol injectable solutions, prepared by mixing paracetamol, water, propylene glycol, and a citrate buffer wherein the concentration of paracetamol is up to 40 mg/ml for exclusive administration by intravenous infusion.

PCT/EP2002/002696 relates to aqueous parenteral solutions of paracetamol containing 1 to 17 grams of paracetamol per liter (i.e. 1 mg per ml to 17 mg per ml) exclusively to be administered by intravenous infusion.

PCT/EP2000/006871 relates to liquid pharmaceutical compositions comprising at least 10% w/v of paracetamol in anhydrous PEG 200. Viscosity of a 22% (w/v) solution Paracetamol as disclosed in example 1 has viscosity 168.4 cps and therefore is unsuitable for use as injectables.

EP2087909 describes ready to use paracetamol injectable solution containing maximum concentration of paracetamil of 1 gm/100 ml in distilled water and buffering agent for exclusive administration as intravenous infusion.

EP0916347 discloses injection solution of paracetamol and combinations of paracetamol with other substances like hyoscine-n-butyl bromide and codeine phosphate Indian Patent Application No. 1746/MUM/2008 relates to a pharmaceutical formulation of paracetamol that provides easy administration to the patients. The above application claims paracetamol injection containing maximum concentration of paracetamol at 15% w/v using combinations of glycofurol and water. However these solutions do not deliver the required therapeutic dose of 500 mg in 2 to 3 ml.

Indian Patent Application No. 1532/DEL/2008 relates to administration of paracetamol through intravenous route in which paracetamol is solubilised in water for injection in combination with passive ingredients like buffers, isotonicity agents, etc. However these also do not provide the required therapeutic dose of 500 mg in 2 to 3 ml.

Indian Patent Application No. 1529/DEL/2008 relates to compositions of paracetamol and ofloxacin for administration through intravenous route employing an aqueous vehicle.

Indian Patent Application No. 1530/DEL/2008 describes compositions of paracetamol and ciprofloxacin in aqueous vehicle to be administered by intravenous route.

Indian Patent Application No.1531/DEL/2008 describes a composition of paracetamol and diclofenac sodium in aqueous vehicle for intravenous administration.

Indian Patent Application No. 2708/DEL/2006 comprises aqueous solution of therapeutic active substances; preferably paracetamol complexed with hydroxyl propyl beta cyclodextrin (HP-B-CD) encapsulated in physiologically and pharmaceutically acceptable oil containing conventional lipophilic surfactant which in turn being dispersed in aqueous medium containing known hydrophilic surfactant.

Indian Patent Application No. 3782/DELNP/2005 relates to a novel injectable formulation of paracetamol, comprising an aqueous solvent, buffering agent with a pKa between 4.5 and 6.5, isotonic agent and dimer of paracetamol wherein the said dimer is used for the stabilization of the formulation.

Indian Patent Application No. 8070/DELNP/2008 relates to an aqueous paracetamol solution for use by perfusion, comprising at least one substance that can react with phenolates.

Paracetamol is sparingly soluble in water, therefore various solvents like propylene glycol, polyethylene glycol 400, glyceryl formal, glycofurol and ethanol etc have been used in the prior art, since paracetamol shows higher solubility in these solvents as compare to water. However there is no prior art disclosing paracetamol injectables with 500 mg of paracetamol in a single dose of about 2 or 3 ml.

A solitary prior art namely IN1746/MUM/2008 reported the use of 44% v/v glycofurol in combination with 10% v/v alcohol (name of alcohol not disclosed) in combination with water to solubuilise a maximum of 150 mg/ml of paracetamol. The same prior art reports the use of 48% v/v glycofurol in combination with water to solubilize a maximum of 150 mg/ml paracetamol. The challenge before the pharmaceutical industry is to provide injections comprising greater than 150 mg/ml up to about 250 mg/ml paracetamol, so that the therapeutic dose of 500 mg can be delivered as an injection of 2 to 3 ml of the solution. Further despite such high concentrations, the injections have to be of viscosity not more than 28 CPS. This has not been achieved to date.

SUMMARY OF THE INVENTION

The main object of the present invention is to provide high concentration parenteral compositions of paracetamol delivering full therapeutic dose of paracetamol, processes for preparing the same and use thereof.

Another object of the present invention is to provide high concentration parenteral compositions of paracetamol delivering therapeutic dose of 500 mg paracetamol in 2 to 3 ml.

Another object of the invention is to provide parenteral compositions of paracetamol containing paracetamol from about 166 mg to 250 mg per ml.

Yet another object of the invention is to provide parenteral compositions containing paracetamol from about 166 to 250 mg per ml in a solvent system comprising glycofurol, ethanol and water.

Yet another object of the invention is to provide parenteral compositions containing paracetamol from about 166 to 250 mg per ml in a solvent system comprising glycofurol, ethanol, polyethylene glycol and water.

Another object of the present invention is to provide a parenteral pharmaceutical formulation of paracetamol or pharmaceutically acceptable salt thereof with viscosity less than 28 CPS, suitable for intramuscular and intravenous administration.

The above and other objects of the present invention are attained according to following preferred embodiments of the present invention. However the scope of the invention is not restricted to the particular embodiments discussed herein after.

In one of the embodiments of the present invention there is provided parenteral pharmaceutical formulations of paracetamol or pharmaceutically acceptable salts thereof, wherein the concentration of the active in a solvent system is >150 mg/ml, the said formulation having viscosity of <28 cps.

In another embodiment of the present invention, there is provided parenteral pharmaceutical formulations of paracetamol or pharmaceutically acceptable salts thereof, wherein the concentration of the active in a solvent system is >150 mg/ml having viscosity of 7 to 28 cps, preferably 7 to 22 cps.

Further, the process for preparation of parenteral compositions of paracetamol or pharmaceutically acceptable salts thereof having the active concentration in the range of about 166 to 250 mg/ml, comprises:
  a. Solubilising the requisite quantities paracetamol or its pharmaceutically acceptable salt thereof in a solvent system under inert atmosphere;
  b. optionally adding antioxidant, chelating agent, benzyl alcohol,
  c. optionally adjusting pH between 4 to 8;
  d. adjusting the volume of the solution to a preset volume;
  e. Filtering the solution through 0.22 micron filter media;
  f. Filling the solution in ampoules/vials under inert atmosphere;
  g. optionally, autoclaving the ampoules/vials.

DETAILED DESCRIPTION OF THE INVENTION

The present invention provides high concentration parenteral compositions of paracetamol or its pharmaceutically acceptable salt thereof comprising full therapeutic dose of paracetamol in a small volume of injection solutions that can be administered by both intramuscular and intravenous routes.

The solubility of paracetamol in various solvents, such as glycofurol, PEG, ethanol, and propylene glycol were determined by us. The solubility of paracetamol in glycofurol, PEG 400, ethanol, propylene glycol and water is about 205 mg/ml, 190 mg/ml, 160 mg/ml, 113 mg/ml and 14 mg/ml respectively. Further, the viscosity of the paracetamol solution in glycofurol at concentration of 205 mg/ml is about 57 CPS which is unacceptable for applications as injectables. As indicated in the earlier sections, the prior art has failed to provide injectables with high concentrations of paracetamol (500 mg in 2 or 3 ml solutions) in any solvent systems. The challenge lies in tailoring the appropriate solvent system to provide injectables containing paracetamol in 166 mg/ml to 250 mg/ml so that the therapeutic dose of paracetamol (500 mg) can be delivered in 2 to 3 ml without compromising in viscosity of these injectables.

We have surprisingly found that substantially high concentration solutions of paracetamol can be prepared without significantly increasing the viscosity, by a judicious combination of solvents to create solvent systems of glycofurol, ethanol and water or solvent systems of glycofurol, ethanol, polyethylene glycol and water. The high concentration of paracetamol achieved in such compositions are significantly higher than those achieved in prior art or in commercially available paracetamol injections.

The concentration of paracetamol achieved in the composition of the present invention range from about 166 mg/ml-250 mg/ml, thereby providing full therapeutic dose of paracetamol as injectable comprising 500 mg in 2 ml-3 ml and 1 gm in 4 ml or 6 ml respectively.

The compositions of the present invention can be administered by intramuscular route, intravenous route or as intravenous infusion after diluting in one of the routinely used intravenous fluids (Dextrose Inj. 5% w/v, Sodium chloride Inj. 0.9% w/v, Pediatric maintenance solution with 5% w/v Dextrose, Sodium chloride Inj. 0.9% w/v & Dextrose 5% w/v, Sodium chloride Inj. 0.45% w/v, Multiple Electrolyte & Dextrose Inj. Type-3, Compound sodium lactate Inj., Dextrose Inj. 10% w/v, Multiple Electrolyte & Dextrose Inj. Type-IV, Multiple Electrolyte & Dextrose Inj. Type-V, Ringer Lactate, etc) as well as after diluting in infusion solutions of antibacterial, antifungal and amoebicidal drugs like ciprofloxacin, ofloxacin, levofloxacin, prazufloxacin, gatifloxacin, moxifloxacin, metronidazole, fluconazole, linezolid, etc.

The compositions of the present invention can also be co-administered as intravenous infusion after diluting the required dose in routinely used intravenous fluids along with anxiolytics (eg. Midazolam injection) or narcotic analgesic (eg. Fentanyl Citrate injection).

The compositions of the present invention may be presented in ampoules/vials containing from about 2 ml to about 3 ml injection solutions or multi-dose vials containing injection solutions that provide multiple doses of paracetamol to deliver 500 mg paracetamol.

In a further aspect, this document discloses a high concentration parenteral composition of paracetamol or its pharmaceutically acceptable salts delivering full therapeutic dose of 500 mg paracetamol in 2-3 ml in an aqueous, stable, and clear solvent system, wherein the solvent system comprises 25-42% v/v glycofurol, greater than 10 to 37% v/v ethanol, water, and optionally polyethylene glycol; wherein the concentration of paracetamol or its pharmaceutically acceptable salts is from 166 mg to 250 mg/ml and the composition has a viscosity in a range of 7-28 CPS at 25° C.

A suitable preservative is optionally incorporated in the compositions.

The compositions of the present invention are capable of being delivered in single dose ampoules/vials containing 500 mg to 2 gm paracetamol for intravenous use.

Accordingly for intravenous administration, 4 or 8 ml of an injection solution containing 250 mg/ml of paracetamol will provide a dose of 1 gram or 2 grams dose of paracetamol respectively. Likewise, 6 or 12 ml of an injection solution containing about 166 mg/ml of paracetamol disclosed herein, will provide 1 gram or 2 grams dose of paracetamol respectively.

Further the amount of paracetamol provided by about 166 mg/ml injection solutions is about 1 gm/6 ml, about 1.5 gm/9 ml, about 2 gm/12 ml. similarly the amount of paracetamol provided by 250 mg/ml injection solutions are about 1 gm/4 ml, about 1.5 mg/6 ml, about 2 gm/8 ml.

Selected pharmaceutical compositions described herein can be injected intramuscularly in the gluteal, deltoid or inner thigh muscles using 22 or 23 gauge needles.

In an embodiment, the parenteral compositions of the present invention comprise paracetamol or its pharmaceutically acceptable salts in a concentration ranging from about 166 to 250 mg/ml solubilized in glycofurol, ethanol and water.

In another embodiment, the parenteral compositions of the present invention comprise paracetamol or its pharmaceutically acceptable salts in a concentration ranging from about 166 to 250 mg/ml solubilized in glycofurol, ethanol, polyethylene glycol and water.

Polyethylene glycol is selected from polyethylene glycol 400/600.

In accordance with another embodiment of the present invention, suitable antioxidant or mixtures thereof is optionally incorporated in the composition.

Suitable antioxidants are selected from Monothioglycerol, Ascorbic Acid, Sodium Ascorbate, Erythorbic Acid, Potassium Metabisulfite, Sodium Metabisulfite, Propionic Acid, Sodium Formaldehyde Sulphoxylate, reduced Gluta-thione, Thiourea, Cysteine, N-aceticysteine, Methionine, Sodium sulfite, Sodium citrate etc.

In yet another embodiment of the present invention chelating agent or mixture thereof is optionally incorporated in the composition.

Suitable chelating agent herein used comprises Trisodium Edetate, Disodium Edetate, Sodium Edetate, Edetate Calcium Disodium, Fumaric Acid, Malic Acid etc.

The injectable solutions of present invention ensure stability of paracetamol during the shelf life.

Further, the injectables produced as per the present invention are clear transparent solutions and upon dilution with one of the routinely used intravenous fluids the solutions remain clear and transparent for at least up to six hours post dilution thereby making them safe for IV administration Further, the compositions of the present invention are compatible with infusion solutions of antibacterial, antifungal and amoebicidal drugs like ciprofloxacin, ofloxacin, levofloxacin, prazufloxacin, gatifloxacin, moxifloxacin, metronidazole, fluconazole, linezolid, etc., and such infusion solutions remain stable, clear and transparent for at least up to six hours post dilution.

Further, the compositions of the present invention produce clear transparent solutions when diluted in routinely used intravenous fluids, along with anxiolytics (Midazolam injection) or narcotic analgesics (Fentanyl Citrate injection etc), and remain stable, clear and transparent for at least up to six hours post dilution.

As mentioned in the section on prior art, commercially available paracetamol injections 150 mg/ml exhibit viscosity of about 25 CPS at 25 degree C. The solitary prior art in which the solution of paracetamol ranging from 60 mg/ml (6% w/v) to 150 mg/ml (15% w/v) have been prepared in glycofurol:ethanol:water (about 44:10:46 or about 4:1:4) and glycofurol: water (48:52 or about 1:1). The viscosity of the examples disclosed in the prior art has not been mentioned in a patent specification and hence the same were prepared by us in our laboratory and the viscosity as per examples 1 and 2 were 13. 5 CPS and 14.8 CPS respectively. It is to be noted that the concentrations of the solutions reported in the said prior art is between 60 mg/ml to 150 mg/ml.

Surprisingly the compositions of present invention in which the concentration of paracetamol is from about 166 to 250 mg per ml, i.e. about 16.6% to 25% w/v (which is significantly higher than any injectable reported in prior art and commercially available product) having viscosity in the range of about 7 to 28 CPS at 25 C. It may further be noted that the judiciously selected solvent system in the present invention enable substantial lowering of viscosity despite significantly higher concentration of paracetamol in the compositions of the present invention as compared to the viscosities of the low concentration solutions reported in the prior art.

In the preferred embodiment, the compositions of the present invention having concentration of paracetamol of about 250 mg/ml enable administrating full therapeutic dose of 500 mg paracetamol in 2 ml injection solution of lower viscosity (about 16 CPS) as compared to viscosity of commercially available 150 mg/ml paracetamol injections as well as compositions disclosed in prior art In another preferred embodiment, the compositions of the present invention having concentration of paracetamol of about 166.66 mg/ml enable administration of full therapeutic dose of 500 mg paracetamol in 3 ml injection solutions of much lower viscosity (7.45 CPS) as compared to commercially available 150 mg/ml paracetamol injections as well as compositions disclosed in prior art The pH of the compositions is in the range of about pH 4 to about pH 8, preferably between pH 5 to pH 7 and more preferably between pH 5.5 to pH 7. In accordance with the invention, the pH of the composition is optionally adjusted to the above values using suitable acid/alkali. Optionally, the pH is adjusted by adding buffering agents to obtain pH between pH 4 to pH 8, preferably between pH 5 to pH 7 and more preferably between pH 5.5 to pH 7.

The acid/alkali is selected from hydrochloric acid, sulphuric acid, acetic acid, citric acid, sodium hydroxide, potassium hydroxide, sodium bicarbonate, potassium bicarbonate, etc A suitable buffer for the compositions comprises a citrate buffer, phosphate buffer and the like.

In one embodiment, the composition of present invention contain about 166 to 200 mg per ml in a solvent system comprising glycofurol 25 to 40% v/v, ethanol 20 to 37% v/v and water (quantity sufficient)

In another embodiment, the composition of present invention contain about 200 to 250 mg per ml in a solvent system comprising glycofurol 25 to 40% v/v, ethanol 23 to 35% v/v and water (quantity sufficient)

In yet another embodiment, the composition of present invention contain about 166 to 200 mg per ml in a solvent system comprising glycofurol 25 to 42% v/v, ethanol 10 to 35% v/v, polyethylene glycol 3 to 19% v/v and water (quantity sufficient)

In yet another embodiment, the composition of present invention contain about 200 to 250 mg per ml in a solvent system comprising glycofurol 30 to 40% v/v, ethanol 24 to 35% v/v, polyethylene glycol 3 to 6% v/v and water (quantity sufficient)

Optionally 2 to 6% v/v benzyl alcohol is incorporated in the compositions.

Optionally antioxidants and chelating agents are incorporated in the compositions.

Optionally buffer, acid/alkali can be incorporated in the compositions.

The solvent system comprising glycofurol, ethanol and water for composition containing about 166 mg/ml to 250 mg/ml contains glycofurol:ethanol:water from about 2.8:2.0:5.1 (example no. 7) to about 1:1:1 (example 12 & 19).

This is in sharp contrast to the ratio of glycofurol and ethanol reported in IN1746/MUM/2008 of 10:1 or a solvent system containing only glycofurol and water.

Viscosity of compositions of present invention having concentration of paracetamol ranging from about 166 mg/ml to 200 mg/ml prepared using solvent system comprising glycofurol, ethanol and water ranges from about 7 to about 16 CPS.

Viscosity of compositions of present invention having concentration of paracetamol ranging from about 200 mg/ml to 250 mg/ml prepared using solvent system comprising glycofurol, ethanol and water ranges from about 16 to about 28 CPS.

Viscosity of compositions of present invention having concentration of paracetamol ranging from about 166 mg/ml to 200 mg/ml prepared using solvent system comprising glycofurol, ethanol, propylene glycol and water ranges from about 9 to about 14 CPS.

Viscosity of compositions of present invention having concentration of paracetamol ranging from about 200 mg/ml to 250 mg/ml prepared using solvent system comprising glycofurol, ethanol, propylene glycol and water ranges from about 14 to about 28 CPS.

The process for preparation of parenteral compositions of paracetamol or pharmaceutically acceptable salts thereof having the active concentration in the range of about 166 to 250 mg/ml, comprises:
  a. Solubilising the requisite quantities paracetamol or its pharmaceutically acceptable salt thereof in a solvent system under inert atmosphere;
  b. optionally adding antioxidant, chelating agent, benzyl alcohol,
  c. optionally adjusting pH between 4 to 8;
  d. adjusting the volume of the solution to a preset volume;
  e. Filtering the solution through 0.22 micron filter media;
  f. Filling the solution in ampoules/vials under inert atmosphere;
  g. optionally, autoclaving the ampoules/vials.

Glycofurol is added to the requisite quantity of ethanol and part of water for injection with stirring under inert gas flushing. The requisite quantity of benzyl alcohol and/or polyethylene glycol 400/600 is optionally added to the above solution followed by addition of the requisite quantity of paracetamol till it completely dissolves. Requisite quantity of antioxidant is added to the above solution. Further requisite of suitable chelating agent and buffer is added and water for injection is added to achieve the required volume. If the pH of the solution is not in the desired range, suitable acid/alkali is added to adjust the pH between 4 to 8. suitable buffer is optionally used to maintain the solution pH 4 and 8. The solution is filtered through 0.2 micron filter and filled into single/multi-dose containers of suitable volumes under inert gas flushing. Optionally the injection solution is sterilized by autoclaving and thereafter filled into single/multi-dose containers of suitable volumes.

In one of the embodiments, the antioxidant when used may be added in the beginning of the process in the solution of glycofural, ethanol and part of injection.

In another embodiment the solvent system of glycofurol, ethanol, polyethylene glycol and part of water for injection is prepared with continuous stirring, under inert gas flushing and polyethylene glycol is not added at any other stage of the process.

In yet another embodiment the solvent system of glycofurol, ethanol, polyethylene glycol and part of water for injection is prepared wherein the antioxidant is dissolved in the part water of injection.

The addition sequence of the ingredients is not restricted to the embodiments disclosed above and a person skilled in the art may arrive at various combination of the compositions disclosed herein.

The following non-limiting examples illustrate in details about the invention. However, they are, not intended to be limiting the scope of present invention in any way

EXAMPLES

The compositions of the present invention are prepared in accordance of the procedure given above and hence not reproduced to avoid repetition.

Example 1

TABLE 1

| Composition of Paracetamol Injection: | | |
|---|---|---|
| S. No. | Ingredients | Amount |
| 1 | Paracetamol | 250 mg |
| 2 | Glycofurol | 0.324 ml |
| 3 | PEG 400 | 0.050 ml |
| 4 | Ethanol | 0.300 ml |
| 5 | Monothioglycerol | 7.50 mg |
| 6 | 1N NaOH solution | q.s. to adjust pH to about 6.5 |
| 7 | Water for injection | q.s. to 1 ml |

The viscosity of injectable solution is 18.59 cps and pH of resultant solution is adjusted to 6.5.

Example 2

TABLE 2

| Composition of Paracetamol injection: | | |
|---|---|---|
| S. No. | Ingredients | Amount |
| 1 | Paracetamol | 250 mg |
| 2 | Glycofurol | 0.324 ml |
| 3 | PEG 400 | 0.050 ml |

TABLE 2-continued

| Composition of Paracetamol injection: | | |
|---|---|---|
| S. No. | Ingredients | Amount |
| 4 | Ethanol | 0.300 ml |
| 5 | Monothioglycerol | 7.50 mg |
| 6 | Disodium hydrogen phosphate | 0.50 mg |
| 7 | Citric acid (5% w/v) | q.s. to adjust pH to about 6.2 |
| 8. | Water for injection | q.s. to 1 ml |

The viscosity of injectable solution is 23.42 cps and pH of resultant solution is adjusted to 6.25.

Example 3

TABLE 3

| Composition of Paracetamol injection: | | |
|---|---|---|
| S. No. | Ingredients | Amount |
| 1 | Paracetamol | 200 mg |
| 2 | Glycofurol | 0.312 ml |
| 3 | PEG 400 | 0.040 ml |
| 4 | Ethanol | 0.240 ml |
| 5 | Monothioglycerol | 7.50 mg |
| 6 | 1N NaOH solution | q.s. to adjust pH to about 6.2 |
| 7 | Water for injection | q.s. to 1 ml |

The viscosity of injectable solution is 14.44 cps and pH of resultant solution is adjusted to 6.20.

Example 4

TABLE 4

| Composition of Paracetamol injection: | | |
|---|---|---|
| S. No. | Ingredients | Amount |
| 1 | Paracetamol | 220 mg |
| 2 | Glycofurol | 0.316 ml |
| 3 | PEG 400 | 0.044 ml |
| 4 | Ethanol | 0.264 ml |
| 5 | Monothioglycerol | 7.50 mg |
| 6 | 1N NaOH solution | q.s. to adjust pH to about 6.2 |
| 7 | Water for injection | q.s. to 1 ml |

The viscosity of injectable solution is 18.76 cps and pH of resultant solution is adjusted to 6.29.

Example 5

TABLE 5

| Composition of Paracetamol Injection: | | |
|---|---|---|
| S. No. | Ingredients | Amount |
| 1 | Paracetamol | 166.66 mg |
| 2 | Glycofurol | 0.280 ml |
| 3 | PEG 400 | 0.033 ml |
| 4 | Ethanol | 0.200 ml |
| 5 | Sodium metabisulphite | 1.5 mg |

TABLE 5-continued

Composition of Paracetamol Injection:

| S. No. | Ingredients | Amount |
| --- | --- | --- |
| 6 | Benzyl alcohol | 0.02 ml |
| 7 | 1N NaOH solution | q.s. to adjust pH to about 6 |
| 8 | Water for injection | q.s. to 1 ml |

The viscosity of injectable solution is 9.02 cps and pH of resultant solution is 5.82.

Example 6

TABLE 6

Composition of Paracetamol injection:

| S. No. | Ingredients | Amount |
| --- | --- | --- |
| 1 | Paracetamol | 166.66 mg |
| 2 | Glycofurol | 0.280 ml |
| 3 | PEG 400 | 0.033 ml |
| 4 | Ethanol | 0.200 ml |
| 5 | Sodium metabisulphite | 1.00 mg |
| 6 | Benzyl alcohol | 0.04 ml |
| 7 | 1N NaOH solution | q.s. to adjust pH to about 6.3 |
| 8 | Water for injection | q.s. to 1 ml |

The viscosity of injectable solution is 10.03 cps and pH of resultant solution is adjusted to 6.31.

Example 7

TABLE 7

Composition of Paracetamol injection:

| S. No. | Ingredients | Amount |
| --- | --- | --- |
| 1 | Paracetamol | 166.66 mg |
| 2 | Glycofurol | 0.279 ml |
| 3 | Ethanol | 0.200 ml |
| 4 | Sodium metabisulphite | 1 mg |
| 5 | Benzyl alcohol | 0.02 ml |
| 6 | Water for injection | q.s. to 1 ml |

The viscosity of injectable solution is 7.45 cps and pH of resultant solution is 5.25.

Example 8

Composition of Paracetamol Injection

TABLE 8

| S. No. | Ingredients | Amount |
| --- | --- | --- |
| 1 | Paracetamol | 200 mg |
| 2 | Glycofurol | 0.312 ml |
| 3 | PEG 400 | 0.040 ml |
| 4 | Ethanol | 0.240 ml |
| 5 | Monothioglycerol | 7.50 mg |
| 6 | Disodium edetate | 0.50 mg |
| 7 | Water for injection | q.s. to 1 ml |

The viscosity of injectable solution is 12.55 cps and pH of resultant solution is adjusted to 6.20.

Example 9

Composition of Paracetamol Injection

TABLE 9

| S. No. | Ingredients | Amount |
| --- | --- | --- |
| 1 | Paracetamol | 200 mg |
| 2 | Glycofurol | 0.300 ml |
| 3 | Ethanol | 0.240 ml |
| 4 | Monothioglycerol | 7.50 mg |
| 5 | Water for injection | q.s. to 1 ml |

The viscosity of injectable solution is 13.40 cps and pH of resultant solution is 5.20.

Example 10

Composition of Paracetamol Injection

TABLE 10

| S. No. | Ingredients | Amount |
| --- | --- | --- |
| 1 | Paracetamol | 200 mg |
| 2 | Glycofurol | 0.320 ml |
| 3 | Ethanol | 0.230 ml |
| 4 | Sodium metabisulphite | 1.0 mg |
| 5 | Water for injection | q.s. to 1 ml |

The viscosity of injectable solution is 13.90 cps and pH of resultant solution is 5.40

Example 11

Composition of Paracetamol Injection

TABLE 11

| S. No. | Ingredients | Amount |
| --- | --- | --- |
| 1 | Paracetamol | 250 mg |
| 2 | Glycofurol | 0.360 ml |
| 3 | PEG 400 | 0.060 ml |
| 4 | Ethanol | 0.300 ml |
| 5 | Monothioglycerol | 7.50 mg |
| 6 | Water for injection | q.s. to 1 ml |

The viscosity of injectable solution is 26.11 cps and pH of resultant solution is adjusted to 6.67.

Example 12

Composition of Paracetamol Injection

TABLE 12

| S. No. | Ingredients | Amount |
| --- | --- | --- |
| 1 | Paracetamol | 166.66 mg |
| 2 | Glycofurol | 0.32 ml |
| 3 | Ethanol | 0.37 ml |
| 4 | Ascorbic acid | 4.0 mg |
| 5 | Water for injection | q.s. to 1 ml |

The viscosity of injectable solution is 10.79 cps and pH of resultant solution is 5.79.

Example 13

Composition of Paracetamol Injection

TABLE 13

| S. No. | Ingredients | Amount |
|---|---|---|
| 1 | Paracetamol | 250 mg |
| 2 | Glycofurol | 0.316 ml |
| 3 | PEG 400 | 0.050 ml |
| 4 | Ethanol | 0.300 ml |
| 5 | Ascorbic acid | 4.0 mg |
| 6 | Water for injection | q.s. to 1 ml |

The viscosity of injectable solution is 16.02 cps and pH of resultant solution is 6.54.

Example 14

Composition of Paracetamol Injection

TABLE 14

| S. No. | Ingredients | Amount |
|---|---|---|
| 1 | Paracetamol | 166.66 mg |
| 2 | Glycofurol | 0.420 ml |
| 3 | PEG 400 | 0.034 ml |
| 4 | Ethanol | 0.201 ml |
| 5 | Monothioglycerol | 7.5 mg |
| 6 | Benzyl alcohol | 0.020 ml |
| 7 | Water for injection | q.s. to 1 ml |

The viscosity of injectable solution is 20.62 cps and pH of resultant solution is 6.30.

Example 15

Composition of Paracetamol Injection

TABLE 15

| S. No. | Ingredients | Amount |
|---|---|---|
| 1 | Paracetamol | 166.6 mg |
| 2 | Glycofurol | 0.251 ml |
| 3 | PEG 400 | 0.188 ml |
| 4 | Ethanol | 0.201 ml |
| 5 | Benzyl alcohol | 0.02 ml |
| 6 | Monothioglycerol | 7.5 mg |
| 7 | Water for injection | q.s. to 1 ml |

The viscosity of injectable solution is 21.55 cps and pH of resultant solution is 6.56

Example 16

Composition of Paracetamol Injection

TABLE 16

| S. No. | Ingredients | Amount |
|---|---|---|
| 1 | Paracetamol | 166.66 mg |
| 2 | Glycofurol | 0.403 ml |
| 3 | Ethanol | 0.10 ml |
| 4 | Monothioglycerol | 7.5 mg |
| 5 | Benzyl alcohol | 0.02 ml |
| 6 | PEG 400 | 0.034 ml |
| 7 | Water for injection | q.s. to 1 ml |

The viscosity of injectable solution is 14.34 cps and pH of resultant solution is 5.84.

Example 17

Composition of Paracetamol Injection

TABLE 17

| S. No. | Ingredients | Amount |
|---|---|---|
| 1 | Paracetamol | 166.66 mg |
| 2 | Glycofurol | 0.422 ml |
| 3 | Ethanol | 0.201 ml |
| 4 | Monothioglycerol | 7.5 mg |
| 5 | Benzyl alcohol | 0.10 ml |
| 6 | PEG 400 | 0.034 ml |
| 7 | Water for injection | q.s. to 1 ml |

The viscosity of injectable solution is 19.12 cps and pH of resultant solution is 6.86.

Example 18

Composition of Paracetamol Injection

TABLE 18

| S. No. | Ingredients | Amount |
|---|---|---|
| 1 | Paracetamol | 250 mg |
| 2 | Glycofurol | 0.35 ml |
| 3 | Ethanol | 0.30 ml |
| 4 | Monothioglycerol | 7.5 mg |
| 5 | Benzyl alcohol | 0.02 ml |
| 6 | PEG 400 | 0.05 ml |
| 7 | Water for injection | q.s. to 1 ml |

The viscosity of injectable solution is 20.92 cps and pH of resultant solution is 6.79.

Example 19

Composition of Paracetamol Injection

TABLE 19

| S. No. | Ingredients | Amount |
|---|---|---|
| 1 | Paracetamol | 250 mg |
| 2 | Glycofurol | 0.38 ml |
| 3 | Ethanol | 0.30 ml |
| 4 | Sodium metabisulphite | 2 mg |
| 5 | Water for injection | q.s. to 1 ml |

The viscosity of injectable solution is 18.70 cps and pH of resultant solution is 5.07

Example 20

Composition of Paracetamol Injection

TABLE 20

| S. No. | Ingredients | Amount |
|---|---|---|
| 1 | Paracetamol | 250 mg |
| 2 | Glycofurol | 0.375 ml |
| 3 | Ethanol | 0.30 ml |
| 4 | Sodium Metabisulphite | 2.0 mg |
| 5 | Water for injection | q.s. to 1 ml |

The viscosity of injectable solution is 18.80 cps and pH of resultant solution is 6.13.

Example 21

The composition of Example-1 as disclosed herein above, was subjected to dilution in routinely used intravenous fluids and infusion solutions of antibacterial, antifungal and amoebicidal drugs as listed in table 21 hereunder. The intravenous fluids containing the diluted composition were assessed to determine their suitability for intravenous infusions.

The following parameters of each of the intravenous fluids were assessed were analyzed, prior to dilution and thereafter at sixty minutes interval, the last analysis being done on completion of six hour:

(i) Clarity of intravenous fluids (see results in table 22)

(ii) pH of the intravenous fluids (see results in table 23)

(iii) Absorbance of the intravenous fluids (see results in table 24)

Further each of the intravenous fluids in which 4 ml of composition (1 gram paracetamol) was diluted, was assessed for analyzed for content of paracetamol, immediately thereafter at sixty minutes interval up to six hours (see results in table 25)

TABLE 21

List of routinely used intravenous fluids and infusion solutions of antibacterial, antifungal and amoebicidal drugs, in which composition as per example 1 was diluted. Each of the intravenous fluids were assigned an alphabetic code number for each of documentation.

| Sr. No | Code No. | Brand name | Solution in which Dilution of Paracetamol Injection 1 gm/4 ml was prepared | Batch No | Mfg Date | Exp Date |
|---|---|---|---|---|---|---|
| 1 | A | TROGYL 100 ML | METRONIDAZOLE INJ IP 0.5% W/V | 12700190 | May 2010 | April 2015 |
| 2 | B | SYSCAN 100 ML | FLUCONAZOLE INJ USP 2 MG/ML | F4610004-A | April 2010 | March 2012 |
| 3 | C | MOXIF IV 100 ML | MOXIFLOXACIN INJ. 4 MG/ML | F6759001-A | February 2009 | January 2011 |
| 4 | D | O-WIN IV 100 ML | OFLOXACIN INJ 2 MG/ML | 9LA34 | January 2009 | February 2011 |
| 5 | E | GATIQUIN 200 ML | GATIFLOXACIN INF. IP 2 MG/ML | ZC9146 | August 2009 | July 2011 |
| 6 | F | DEXTROSE INJ 250 ML | DEXTROSE INJ IP 5% W/V | 907 005 | July 2009 | June 2012 |
| 7 | G | SODIUM CHLORIDE 250 ML | SODIUM CHLORIDE INJ 0.9% W/V | 801093 | January 2008 | December 2010 |
| 8 | H | DENILYTE 'P 250 ML | PEDIATRIC MAINTANCE SOLUTION WITH 5% DEXTROSE (MULTIPLE ELECTROLYTE & DEXTROSE INJ TYPE-1 IP) | 906048 | June 2009 | May 2012 |
| 9 | I | NS | SODIUM CHLORIDE INJ 0.9% W/V | 30600571 | May 2010 | February 2015 |
| 10 | J | DNS | SODIUM CHLORIDE INJ 0.9% W/V & DEXTROSE 5% | 31701197 | June 2010 | May 2013 |
| 11 | K | NIRLYTE-P | MULTIPLE ELECTROLYTE & DEXTROSE INJ TYPE-1 IP | 302622699 | May 2010 | April 2013 |
| 12 | L | Sodium Chloride Injection 500 Ml | SODIUM CHLORIDE INJ 0.45% W/V IP | 1007 987 | July 2010 | June 2013 |
| 13 | M | 5D | DEXTROSE INJ IP 5% W/V | A18592 | September 2008 | August 2013 |
| 14 | N | B.BRAUN | MULTIPLE ELECTROLYTE & DEXTROSE INJ TYPE-3 IP | AJ8617 | October 2008 | September 2013 |
| 15 | O | RL | COMPOUND SODIUM LACTATE INJ IP | AL7791 | December 2007 | November 2012 |
| 16 | P | 10D | DEXTROSE INJ IP 10% W/V | 811 069 | November 2008 | October 2011 |
| 17 | Q | CIPLOX | CIPROFLOXACIN INJ IP 2 MG/ML | XR9017 | July 2009 | June 2012 |
| 18 | R | DENILYTE 'G' 500 ML | MULTIPLE ELECTROLYTES & DEXTROSE INJ TYPE-IV IP | 1003 340 | March 2010 | February 2013 |
| 19 | S | DENILYTE 'E' 500 ML | MULTIPLE ELECTROLYTES & DEXTROSE INJ TYPE-V IP | 909 015 | October 2010 | August 2012 |
| 20 | T | Compound Sodium Lactate Inj IP 250 ml | COMPOUND SODIUM LACTATE INJ IP | 902 010 | February 2009 | January 2012 |

TABLE 22

Clarity of Intravenous fluids before and after dilution

| S. No | Solution Identifier | Before Dilution (Initial) | After 1 hr Dilution | After 2 hr Dilution | After 3 hr Dilution | After 4 hrs Dilution | After 5 Hrs Dilution | After 6 Hrs Dilution |
|---|---|---|---|---|---|---|---|---|
| 1 | A | Clear | Clear | Clear | Clear | Clear | Clear | Clear |
| 2 | B | Clear | Clear | Clear | Clear | Clear | Clear | Clear |
| 3 | C | Clear | Clear | Clear | Clear | Clear | Clear | Clear |
| 4 | D | Clear | Clear | Clear | Clear | Clear | Clear | Clear |
| 5 | E | Clear | Clear | Clear | Clear | Clear | Clear | Clear |
| 6 | F | Clear | Clear | Clear | Clear | Clear | Clear | Clear |
| 7 | G | Clear | Clear | Clear | Clear | Clear | Clear | Clear |
| 8 | H | Clear | Clear | Clear | Clear | Clear | Clear | Clear |
| 9 | I | Clear | Clear | Clear | Clear | Clear | Clear | Clear |
| 10 | J | Clear | Clear | Clear | Clear | Clear | Clear | Clear |
| 11 | K | Clear | Clear | Clear | Clear | Clear | Clear | Clear |
| 12 | L | Clear | Clear | Clear | Clear | Clear | Clear | Clear |
| 13 | M | Clear | Clear | Clear | Clear | Clear | Clear | Clear |
| 14 | N | Clear | Clear | Clear | Clear | Clear | Clear | Clear |
| 15 | O | Clear | Clear | Clear | Clear | Clear | Clear | Clear |
| 16 | P | Clear | Clear | Clear | Clear | Clear | Clear | Clear |
| 17 | Q | Clear | Clear | Clear | Clear | Clear | Clear | Clear |
| 18 | R | Clear | Clear | Clear | Clear | Clear | Clear | Clear |
| 19 | S | Clear | Clear | Clear | Clear | Clear | Clear | Clear |
| 20 | T | Clear | Clear | Clear | Clear | Clear | Clear | Clear |

TABLE 23 pH of Intravenous fluids before and after dilution

| S. No | Solution Identifier | Before Dilution (Initial) | After 1 hr Dilution | After 2 hr Dilution | After 3 hr Dilution | After 4 hrs Dilution | After 5 Hrs Dilution | After 6 Hrs Dilution |
|---|---|---|---|---|---|---|---|---|
| 1 | A (pH limit 4.5 to 7.0) | 5.52 | 5.44 | 5.42 | 5.39 | 5.38 | 5.36 | 5.42 |
| 2 | B (pH limit 4.0 to 8.0) | 5.62 | 5.42 | 5.43 | 5.29 | 5.30 | 5.32 | 527 |
| 3 | C | 4.83 | 4.89 | 4.91 | 4.94 | 4.95 | 4.96 | 4.92 |
| 4 | D (pH limit 3.8 to 5.8) | 5.27 | 5.32 | 5.33 | 5.42 | 5.44 | 5.48 | 5.40 |
| 5 | E (pH limit 3.5 to 5.5) | 4.92 | 4.96 | 4.95 | 4.94 | 4.95 | 4.92 | 4.91 |
| 6 | F (pH limit 3.5 to 6.5) | 4.36 | 4.32 | 4.33 | 4.41 | 4.42 | 4.43 | 4.42 |
| 7 | G (pH limit 4.5 to 7.5) | 6.52 | 6.47 | 6.50 | 6.48 | 6.47 | 6.45 | 6.45 |
| 8 | H pH limit 3.5 to 6.5 | 5.51 | 5.52 | 5.55 | 5.49 | 5.48 | 5.42 | 5.47 |
| 9 | I pH limit 4.5b to 7.5 | 5.49 | 5.49 | 5.51 | 5.65 | 5.66 | 5.61 | 5.61 |
| 10 | J pH limit 3.5 to 6.5 | 4.26 | 4.36 | 4.33 | 4.34 | 4.32 | 4.38 | 4.32 |
| 11 | K pH limit 3.0 to 7.0 | 5.59 | 5.58 | 5.55 | 5.62 | 5.6 | 5.65 | 5.63 |
| 12 | L pH limit 4.5 to 7.5 | 5.93 | 5.87 | 5.92 | 5.79 | 5.72 | 5.78 | 5.75 |
| 13 | M pH limit 3.5 to 6.5 | 4.26 | 4.52 | 4.53 | 4.54 | 4.55 | 4.59 | 4.55 |
| 14 | N pH limit 3.0 to 7.0 | 5.43 | 5.48 | 5.49 | 5.45 | 5.46 | 5.51 | 5.46 |
| 15 | O pH limit 4.0 to 6.5 | 5.41 | 5.39 | 5.36 | 5.35 | 5.34 | 5.31 | 5.34 |
| 16 | P pH limit 3.5 to 6.5 | 3.91 | 3.99 | 3.96 | 4.02 | 3.99 | 3.98 | 4.05 |
| 17 | Q pH limit 3.5 to 4.6 | 4.01 | 4.02 | 4.03 | 4.02 | 4.03 | 4.06 | 4.03 |
| 18 | R pH limit 3.5 to 7.0 | 3.67 | 3.64 | 3.63 | 3.59 | 3.58 | 3.59 | 3.56 |
| 19 | S pH limit 3.5 to 7.0 | 5.51 | 5.52 | 5.52 | 5.49 | 5.50 | 5.52 | 5.47 |
| 20 | T pH limit 4.0 to 6.5 | 5.94 | 5.91 | 5.90 | 5.87 | 5.84 | 5.86 | 5.83 |

TABLE 24

Absorbance of Intravenous fluids before and after dilution

| Sr. No | Solution identifier | Before Dilution (Initial) | After 1 hr Dilution | After 2 hr Dilution | After 3 hr Dilution | After 4 hrs Dilution | After 5 Hrs Dilution | After 6 Hrs Dilution |
|---|---|---|---|---|---|---|---|---|
| 1 | A | 0.023 | 0.074 | 0.075 | 0.074 | 0.073 | 0.073 | 0.072 |
| 2 | B | 0.002 | 0.002 | 0.006 | 0.002 | 0.001 | 0.001 | 0.002 |
| 3 | C | 2.601 | 2.356 | 2.353 | 2.310 | 2.329 | 2.329 | 2.304 |
| 4 | D | 0.136 | 0.112 | 0.113 | 0.107 | 0.107 | 0.108 | 0.112 |
| 5 | E | 0.046 | 0.040 | 0.040 | 0.041 | 0.039 | 0.040 | 0.045 |
| 6 | F | 0.002 | 0.008 | 0.009 | 0.008 | 0.007 | 0.004 | 0.006 |

TABLE 24-continued

Absorbance of Intravenous fluids before and after dilution

| Sr. No | Solution identifier | Before Dilution (Initial) | After 1 hr Dilution | After 2 hr Dilution | After 3 hr Dilution | After 4 hrs Dilution | After 5 Hrs Dilution | After 6 Hrs Dilution |
|---|---|---|---|---|---|---|---|---|
| 7 | G | 0.002 | 0.008 | 0.005 | 0.006 | 0.007 | 0.005 | 0.006 |
| 8 | H | 0.014 | 0.001 | 0.004 | 0.006 | 0.005 | 0.005 | 0.006 |
| 9 | I | 0.008 | 0.005 | 0.006 | 0.003 | 0.008 | 0.005 | 0.003 |
| 10 | J | 0.001 | 0.003 | 0.003 | 0.004 | 0.003 | 0.002 | 0.003 |
| 11 | K | 0.009 | 0.001 | 0.003 | 0.003 | 0.004 | 0.003 | 0.002 |
| 12 | L | 0.00 | 0.00 | 0.00 | 0.001 | 0.001 | 0.002 | 0.001 |
| 13 | M | 0.002 | 0.000 | 0.002 | 0.001 | 0.003 | 0.003 | 0.005 |
| 14 | N | 0.008 | 0.009 | 0.006 | 0.005 | 0.004 | 0.006 | 0.005 |
| 15 | O | 0.004 | 0.006 | 0.001 | 0.001 | 0.002 | 0.001 | 0.004 |
| 16 | P | 0.012 | 0.009 | 0.015 | 0.014 | 0.013 | 0.009 | 0.010 |
| 17 | Q | 0.008 | 0.010 | 0.016 | 0.011 | 0.014 | 0.016 | 0.012 |
| 18 | R | 0.006 | 0.003 | 0.002 | 0.005 | 0.004 | 0.002 | 0.002 |
| 19 | S | 0.026 | 0.027 | 0.027 | 0.028 | 0.031 | 0.026 | 0.027 |
| 20 | T | 0.001 | 0.003 | 0.006 | 0.004 | 0.005 | 0.003 | 0.006 |

TABLE 25

Assay of paracetamol

| Sr. No. | Solution identifier | After 1 hrs | After 2 hrs | After 3 hrs | After 4 hrs | After 5 hrs | After 6 hrs |
|---|---|---|---|---|---|---|---|
| 1 | A | 99.8 | 99.47 | 99.32 | 101.33 | 99.51 | 98.57 |
| 2 | B | 100.7 | 100.89 | 101.91 | 101.88 | 101.58 | 99.41 |
| 3 | C | 99.8 | 99.12 | 100.41 | 98.94 | 99.95 | 100.39 |
| 4 | D | 100.65 | 100.53 | 99.72 | 99.99 | 99.82 | 100.47 |
| 5 | E | 98.81 | 100.95 | 99.16 | 99.39 | 99.5 | 97.71 |
| 6 | F | 96.19 | 97.88 | 96.76 | 95.31 | 95.28 | 96.39 |
| 7 | G | 101.5 | 101.4 | 101.01 | 101.09 | 101.32 | 101.08 |
| 8 | H | 99.39 | 98.55 | 99.03 | 98.84 | 99.03 | 98.27 |
| 9 | I | 98.96 | 98.37 | 99.28 | 98.67 | 98.26 | 98.22 |
| 10 | J | 99.54 | 98.68 | 99.96 | 98.86 | 98.44 | 100.06 |
| 11 | K | 97.73 | 97.41 | 98.27 | 99.95 | 98.27 | 98.78 |
| 12 | L | 99.37 | 98.31 | 99.43 | 99.78 | 99.84 | 98.54 |
| 13 | M | 98.36 | 98.03 | 98.01 | 97.79 | 98.11 | 97.99 |
| 14 | N | 98.89 | 99.67 | 99.79 | 99.57 | 99.71 | 99.51 |
| 15 | O | 98.90 | 99.71 | 98.36 | 98.98 | 99.14 | 99.04 |
| 16 | P | 98.56 | 98.43 | 98.45 | 99.03 | 98.40 | 98.06 |
| 17 | Q | 101.51 | 101.4 | 101.88 | 101.99 | 100.73 | 101.56 |
| 18 | R | 102.36 | 102.3 | 102.72 | 101.4 | 101.62 | 100.94 |
| 19 | S | 99.58 | 99.33 | 99.19 | 98.6 | 99.14 | 99.41 |
| 20 | T | 101.31 | 100.52 | 100.62 | 100.71 | 100.7 | 100.76 |

CONCLUSION

On examining the above tables, one can conclude that:
a) There is no significant change in the clarity, pH and absorbance values of the intravenous fluids, when 4 ml of the composition as per example 1 is diluted in the intravenous fluids.
b) Assay of paracetamol does not show any significant decrease even after six hours of dilution of the compositions in intravenous fluid.

We claim:

1. A high concentration parenteral composition of paracetamol or its pharmaceutically acceptable salts delivering full therapeutic dose of 500 mg paracetamol in 2-3 ml in an aqueous, stable, and clear solvent system, wherein the solvent system comprises
25 to 42% v/v glycofurol,
greater than 10 to 37% v/v ethanol,
water, and
optionally polyethylene glycol;
wherein the concentration of paracetamol or its pharmaceutically acceptable salts is from 166 mg to 250 mg/ml and the composition has a viscosity in a range of 7-28 CPS at 25° C.

2. The high concentration parenteral composition of paracetamol or its pharmaceutically acceptable salts as claimed in claim 1, wherein the viscosity is in a range of 16-28 CPS.

3. The high concentration parenteral composition of paracetamol or its pharmaceutically acceptable salts as claimed in claim 1, wherein the composition contains paracetamol in a concentration from 166 to 200 mg/ml in a solvent system, the solvent system comprising:
25 to 40% v/v glycofurol,
20 to 37% v/v ethanol, and
a volume of water to make the total volume of the composition a maximum of 2-3 ml.

4. The high concentration parenteral composition of paracetamol or its pharmaceutically acceptable salts as claimed in claim 3, wherein the viscosity of the composition is in a range of 7 to about 16 CPS.

5. The high concentration parenteral composition of paracetamol or its pharmaceutically acceptable salts as claimed in claim 1, wherein the composition contains paracetamol in a concentration from 200 to 250 mg/ml in a solvent system, the solvent system comprising:
25 to 40% v/v glycofurol,
23 to 35% v/v ethanol and
a volume of water to make the total volume of the composition a maximum of 2-3 ml.

6. The high concentration parenteral composition of paracetamol or its pharmaceutically acceptable salts as claimed in claim 5 wherein the viscosity of the composition is in a range of 16 to 28 CPS.

7. The high concentration parenteral composition of paracetamol or its pharmaceutically acceptable salts as claimed in claim 1, wherein the composition contains paracetamol in a concentration from 166 to 200 mg/ml in a solvent system, the solvent system comprising:
25 to 42% v/v glycofurol,
greater than 10 to 35% v/v ethanol,
3 to 19% v/v polyethylene glycol and
a volume of water to make the total volume of the composition a maximum of 2-3 ml.

8. The high concentration parenteral composition of paracetamol or its pharmaceutically acceptable salts as claimed in claim 7, wherein the viscosity of the composition is in a range of 9 to 14 CPS.

9. The high concentration parenteral composition of paracetamol or its pharmaceutically acceptable salts as claimed in claim 7, wherein the polyethylene glycol is selected from one of: polyethylene glycol 400 and polyethylene glycol 600.

10. The high concentration parenteral composition of paracetamol or its pharmaceutically acceptable salts as claimed in claim 1, wherein the composition contains paracetamol in a concentration from 200 to 250 mg/ml in a solvent system, the solvent system comprising:
   30 to 40% v/v glycofurol,
   24 to 35% v/v ethanol,
   3 to 6% v/v polyethylene glycol and
   a volume of water to make the total volume of the composition a maximum of 2-3 ml.

11. The high concentration parenteral composition of paracetamol or its pharmaceutically acceptable salts as claimed in claim 10, wherein the viscosity of the composition is in a range of 14 to 28 CPS.

12. The high concentration parenteral composition of paracetamol or its pharmaceutically acceptable salts as claimed in claim 10, wherein the polyethylene glycol is selected from one of: polyethylene glycol 400 and polyethylene glycol 600.

13. The high concentration parenteral composition of paracetamol or its pharmaceutically acceptable salts as claimed in claim 1, wherein the solvent system comprises a polyethylene glycol selected from one of: polyethylene glycol 400 and polyethylene glycol 600.

14. The high concentration parenteral composition of paracetamol or its pharmaceutically acceptable salts as claimed in claim 1, wherein the composition further comprises at least one of: antioxidants, chelating agents and buffering agents.

15. The high concentration parenteral composition of paracetamol or its pharmaceutically acceptable salts as claimed in claim 1, wherein the composition further comprises 2 to 6% v/v benzyl alcohol.

* * * * *

UNITED STATES PATENT AND TRADEMARK OFFICE
CERTIFICATE OF CORRECTION

PATENT NO. : 9,616,128 B2
APPLICATION NO. : 13/806541
DATED : April 11, 2017
INVENTOR(S) : Patel et al.

Page 1 of 1

It is certified that error appears in the above-identified patent and that said Letters Patent is hereby corrected as shown below:

In the Specification

Column 4, Line 67 should read:
In a further aspect, this document discloses a high concentration parenteral composition of paracetamol or its pharmaceutically acceptable salts delivering full therapeutic dose of 500 mg paracetamol in 2-3 ml in an aqueous, stable, and clear solvent system, wherein the solvent system comprises 25-42% v/v glycofurol, greater than 10 to 37% v/v ethanol, water, and optionally polyethylene glycol; wherein the concentration of paracetamol or its pharmaceutically acceptable salts is from 166 mg to 250 mg/ml and the composition has a viscosity in a range of 7-28 CPS at 25°C.

Column 5, Line 65 delete:
In a further aspect, this document discloses a high concentration parenteral composition of paracetamol or its pharmaceutically acceptable salts delivering full therapeutic dose of 500 mg paracetamol in 2-3 ml in an aqueous, stable, and clear solvent system, wherein the solvent system comprises 25-42% v/v glycofurol, greater than 10 to 37% v/v ethanol, water, and optionally polyethylene glycol; wherein the concentration of paracetamol or its pharmaceutically acceptable salts is from 166 mg to 250 mg/ml and the composition has a viscosity in a range of 7-28 CPS at 25°C.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*